US00PP12523P2

(12) United States Plant Patent
Olesen et al.

(10) Patent No.: US PP12,523 P2
(45) Date of Patent: Apr. 9, 2002

(54) FLORIBUNDA ROSE PLANT NAMED 'POULOMA'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/282,070

(22) Filed: Mar. 29, 1999

(51) Int. Cl.[7] ..... A01H 5/00
(52) U.S. Cl. ..... Plt./148
(58) Field of Search ..... Plt./148, 149, 107

(56) References Cited

PUBLICATIONS

EF–SORTSBESKYTTELSESATTEST, EU1527, Dec. 16, 1996, 6 pages.*

European Union Community Plant Variety Office, 0602/95, 7 pages.*

Republic of South Africa, Certificate of Grant of A Plant Breeders Right, Mar. 31, 1999.*

UPOV–ROM, May 2000, Plant Variety Database, GTI Jouve Retrieval Software, 3 citations for 'POULoma'.*

* cited by examiner

*Primary Examiner*—Howard J. Locker

(57) ABSTRACT

A new garden rose plant which has abundant, shell pink flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an unnamed seedling and 'The Fairy'. The two parents were crossed and the resulting seeds were planted in a controlled environment. The new variety is named 'POULoma'.

The new rose may be distinguished from its seed parent, an unnamed seedling, by the following combination of characteristics:

1. The seed parent has darker pink blooms than 'POULoma';

2. The seed parent blooms are semi-double; whereas, 'POULoma' has very double blooms;

3. The seed parent is lower growing than 'POULoma'.

The new variety may be distinguished from its pollen parent, 'The Fairy', by the following combination of characteristics:

1. The blooms of the seed parent are much smaller than the blooms of 'POULoma';

2. The pollen parent blooms in trusses along the stem; whereas, 'POULoma' has clusters of blooms located at the end of the flowering stem.

The objective of the hybridization of this rose variety for nursery and garden use was to create a new and distinct variety with unique qualities, such as:

1. Uniform and abundant flowers;

2. Vigorous, compact growth;

3. Old-fashioned rosette style flowers;

4. Continuous blooming.

This combination of qualities is not present in previously available commercial cultivars of this type and distinguishes 'POULoma' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULoma' was selected in the spring of 1983 by the inventors as a single plant from the progeny of the aforementioned hybridization.

Asexual reproduction of 'POULoma' by traditional budding was first done by L. Pernille and Mogens N. Olesen in August, 1983 in Fredensborg, Denmark. This initial and other subsequent propagations conducted in controlled environments have demonstrated that the characteristics of 'POULoma' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULoma'. Specifically illustrated in SHEET 1:

1. Stem of plant showing branching and the attachment of leaves, buds, and peduncles;
2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a description of 'POULoma', as observed in its outdoor growth in a field nursery in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULoma', a shrub rose variety, from the same inventors, described and illustrated in U.S. Plant Pat. No. 9,261 and issued on Aug. 29, 1995 are compared to 'POULoma' in Chart 1.

CHART 1

| | 'POULoma' | 'POULma' |
|---|---|---|
| Color of upper surface of open bloom. | Red Group 48C. | Red Group 62C. |
| Petalage. | Very Double 75–85 petals. | Very Double, 110–120. |
| Height of plant. | 110 cm. | 60 cm. |

Parents:
*Seed parent.*—Unnamed seedling.
*Pollen parent.*—'The Fairy'.
Classification:
*Botanical.*—*Rosa hybrida.*
*Commercial.*—Floribunda.

FLOWER AND FLOWER BUD

Blooming habit: Continuous.
Flower bud:
*Size.*—Upon opening, 35 mm in length from base of receptacle to end of bud.
*Bud form.*—Medium, pointed ovoid.
*Bud color.*—As sepals unfold, Red Group 50B. Red Group 52C at ¼ opening.
*Sepals.*—Yellow-Green Group 144A. Weak foliaceous appendages on three of the five sepals. Surfaces of sepals moderately pubescent on interior and exterior. Stipitate glands are very limited in number and are located primarily on margins, although a few are observed on exterior of sepal.
*Receptacle.*—Surface: Pubescent with few stipitate glands. Shape: Urn-shaped. Size: Small, 5 mm (h)×4 mm (w). Color: Yellow-Green Group 146 with anthocyanin of Greyed-Red Group 180A.
*Peduncle.*—Surface: Large number of stipitate glands. Length: 40 mm to 60 mm average length. Color: Yellow-Green Group 146C, with intonations of Greyed-Purple Group 184C. Strength: Upright.
*Borne.*—Generally Multiple buds per stem, with 2–5 buds per Flowering stem.
Flower bloom:
*Fragrance.*—Very light, floral scent.
*Duration.*—As a cut flower 2 to 4 days. The blooms have a duration on the plant of approximately 4 to 5 days. Petals fall cleanly away from plant.
*Size.*—Average flower diameter is 75 mm when open.
*Form.*—Rosette to nearly quartered form.
*Shape of flower when viewed from the side.*—Upon opening, upper part: Flat. Upon opening, lower part: Flattened convex. Open flower, upper part: Flattened convex. Open flower, lower part: Concave.
*Petalage.*—Very double, 75–85 petals under normal conditions with 4–8 petaloids.
Color:
*Upon opening.*—Outermost petals: Upper Surface: Red Group 52C. Reverse Side: Red Group 54C. Innermost petals: Upper Surface: Red Group 52C. Reverse Side: Red Group 52B.
*Upon opening, basal petal spots.*—Outermost petals: Outer Side: Green-Yellow Group 1B. Inner Side: Green-Yellow Group 1B. Innermost petals: Outer Side: Green-Yellow Group 1B. Inner Side: Green-Yellow Group 1B.
*After opening.*—Outermost petals: Upper Surface: Red Group 55B. Reverse Side: Red Group 55B. Innermost petals: Upper Surface: Red Group 48C. Reverse Side: Red Group 48A.
*After opening, basal petal spots.*—Outermost petals: Outer Side: Yellow-Green Group 154C. Inner Side: Yellow-Green Group 154C. Innermost petals: Outer Side: Yellow-Green Group 154A. Inner Side: Yellow-Green Group 154A.
General tonality: On open flower Red Group 55C. Flowers hold this color until petals drop.
Petals:
*Petal reflex.*—Somewhat.
*Petal edge.*—Uniform.
*Shape.*—Deltoid shape.
*Petaloids.*—Present. Quantity: 4–8.
*Thickness.*—Average.
*Arrangement.*—Informal.
Reproductive organs:
*Pollen.*—Color: Yellow-Orange Group 17B. Quantity: Limited.
*Anthers.*—Size: Large. Color: Orange Group 26D. Quantity: Average.
*Filaments.*—Color: Yellow-Green Group 154B.
*Stigmas.*—Substantially superior to anthers. Anthers are more horizontal then upright. Color: Orange Group 19B, with intonations of Red Group 47B.
*Styles.*—Color: Yellow-Green Group 149C.
*Hips.*—None observed.

PLANT

Plant growth: Vigorous, bushy. When grown as a budded field grown plant on *Rosa multiflora* understock, the average height of the plant itself is 110 cm and the average width is 100 cm.
Stems:
*Characteristic flowering stem length.*—70 cm. Color: Young wood: Yellow-Green Group 144B. Older wood: Yellow-Green Group 144B. Thorns: Incidence: Moderate. Size: Average length: 9 mm. Color: Greyed-Orange Group 146A. Shape: Concave. Surface: Young wood: Smooth. Older wood: Smooth.
Plant foliage: Normal number of leaflets on leaves in middle of the stem: 5–7 leaflets. 7 leaves are common.
*Leaf size.*—Medium, 100 mm (l)×60 mm (w).
*Quantity.*—Average.
*Color.*—Upper Leaf Surface: Yellow-Green Group 147A. Lower Leaf Surface: Yellow-Green Group 147B. Juvenile foliage: Upper Surface: Yellow-Green Group 147A, with intonations of Greyed- Purple Group 184C. Lower Surface: Yellow-Green Group 147A, with intonations of Greyed-Purple Group 184C.

*Anthocyanin*.—Location: New stems, thorns, stipules, margins of leaflets and buds. Color: Greyed-Purple Group 184C.

Plant leaves and leaflets:

*Stipules*.—Size: 12–15 mm (l)×4–5 mm (w). Color: Yellow-Green Group 146D. Stipitate glands: Limited number on margins.

*Petiole*.—Length: 30 mm. Color: Yellow-Green Group 146D. Underneath: Smooth, no stipitate gland or prickles observed. Margins: Small number of fine stipitate glands.

*Rachis*.—Color: Yellow-Green Group 146C. Underneath: Prickles where the leaflets join rachis on mature foliage. On juvenile foliage rachis is smooth. Margins: Small fine stipitate glands on margins.

*Leaflet*.—Edge: Serrated. Shape: Broadly Ovate. Texture: Moderate glossy, thick.

Disease resistance: Average resistance to mildew, black spot, and Botrytis under normal growing conditions in Jackson County, Oreg.

Cold Hardiness: 'POULoma' has been found to be cold hardy in Denmark and Jackson County, Oreg.

We claim:

1. A new and distinct variety of rose plant of the floribunda class, substantially as herein illustrated and described as a distinct and novel rose variety due to its abundant, shell pink flowers, vigorous growth and extended period of bloom.

* * * * *

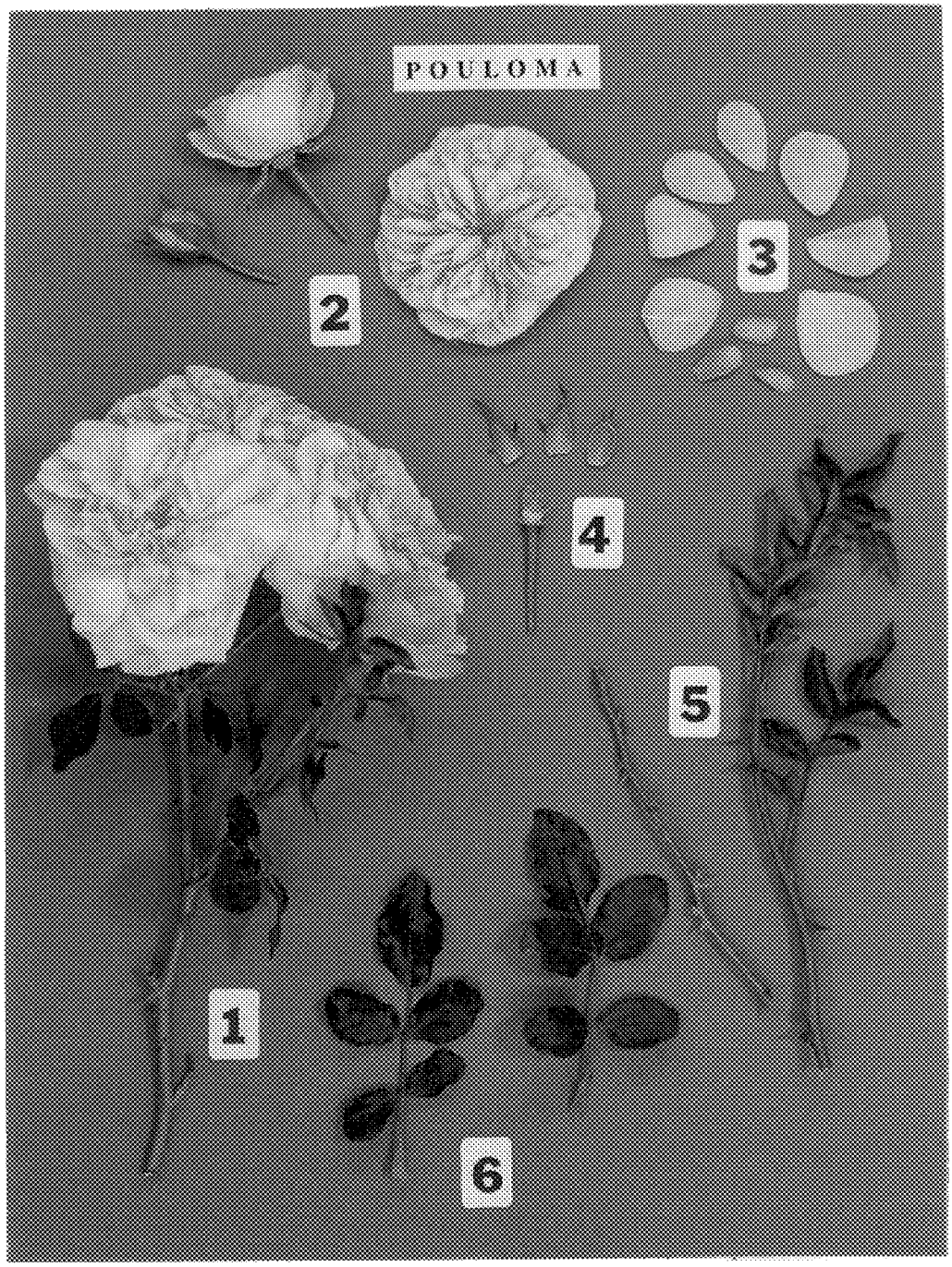
POULOMA
2
3
4
5
1
6